United States Patent [19]

Kubo et al.

[11] Patent Number: 6,043,370

[45] Date of Patent: Mar. 28, 2000

[54] METHOD FOR PRODUCING ARYLAMINE

[75] Inventors: Shinji Kubo; Taichi Shintou, both of Kanagawa, Japan

[73] Assignee: Sankio Chemical Co., Ltd., Tokyo, Japan

[21] Appl. No.: 09/132,230

[22] Filed: Aug. 11, 1998

[30] Foreign Application Priority Data

Aug. 25, 1997 [JP] Japan .................................. 9-228366
Nov. 19, 1997 [JP] Japan .................................. 9-318401
Jan. 9, 1998 [JP] Japan ................................ 10-003266
Jan. 9, 1998 [JP] Japan ................................ 10-003298

[51] Int. Cl.$^7$ ................................................. C07C 209/10
[52] U.S. Cl. ........................... 546/257; 564/309; 564/405
[58] Field of Search ................................. 564/309, 405; 546/257

[56] References Cited

U.S. PATENT DOCUMENTS

| | | | |
|---|---|---|---|
| 5,648,539 | 7/1997 | Goodbrand | 564/309 |
| 5,648,542 | 7/1997 | Goodbrand | 564/405 |
| 5,654,482 | 8/1997 | Goodbrand | 564/405 |
| 5,705,697 | 1/1998 | Goodbrand | 564/405 |
| 5,723,669 | 3/1998 | Goodbrand | 564/307 |
| 5,723,671 | 3/1998 | Goodbrand | 564/307 |

*Primary Examiner*—Zinna Northington Davis
*Attorney, Agent, or Firm*—Sughrue, Mion, Zinn, Macpeak & Seas, PLLC

[57] ABSTRACT

A method for the production of arylamine is described, which comprises allowing an aromatic amine to react with an aromatic halide in the presence of a copper-containing catalyst in a reaction solvent having an ionization potential of from 8.0 to 9.0 eV. According to the method of this invention, an arylamine, in particular a triarylamine or diarylamine, useful as a raw material for use in electronic materials or as an intermediate thereof can be produced with a high purity and in a high yield or at a low cost.

13 Claims, No Drawings

METHOD FOR PRODUCING ARYLAMINE

FIELD OF THE INVENTION

This invention relates to a method for the production of an arylamine, in particular a triarylamine or diarylamine, useful as a raw material for use in electronic materials or as an intermediate thereof, with a high purity and in a high yield or at a low cost.

BACKGROUND OF THE INVENTION

The reaction of the present invention is included in a category of reaction classified as the Ullmann condensation reaction.

The Ullmann condensation reaction has been discovered by F. Ullmann (*Chem. Ber.*, 36, 2382 (1903)) in which an aromatic amine and an aromatic halogen compound, preferably an aromatic iodide compound, are subjected to a coupling reaction in the presence of a base and a copper catalyst.

In the prior art, an alkylbenzene, a halogenobenzene, nitrobenzene or the like aromatic compound, or decane, tridecane or the like saturated aliphatic hydrocarbon compound, having an ionization potential of 9.1 eV or more is used as the solvent in this reaction.

In addition, cyclic nitrogen-containing compounds such as pyridines, quinolines and the like are used as the reaction solvent as a means for accelerating the reaction (for example, *Tetrahedron Lett.*, 4531 (1965), *Tetrahedron Lett.*, 679 (1966)).

However, the aforementioned reaction in which an aromatic compound or a saturated aliphatic hydrocarbon compound is used as the solvent generally takes a prolonged period of reaction time and requires a considerably high temperature for achieving practical arylation rate, thus posing a problem in that by-products are formed due to oxidation of substituent groups and dimerization of the formed product.

Also, in the case of the use of cyclic nitrogen-containing compounds such as pyridines, quinolines and the like as the reaction solvent as a means for accelerating the reaction, the problem of causing by-product formation is still unsolved.

In addition, since separation and purification of such by-products are extremely difficult, high degree purification of the arylamine with the aim of using it as a raw material for electronic material use or as an intermediate thereof causes problems in that its production yield is reduced or the product is not practical due to high cost.

As described in the foregoing, a practical method for producing an arylamine with a high purity and in a high yield or at a low cost has not been developed yet.

SUMMARY OF THE INVENTION

In view of the above, it therefore becomes an object of the present invention to, by resolving the aforementioned problems involved in the prior art, provide a novel method by which a high purity arylamine, in particular a triarylamine or diarylamine, can be produced in a high yield or at a low cost.

Accordingly, the object of the present invention is realized by:

(1) a method for producing arylamine which comprises allowing an aromatic amine to react with an aromatic halide in the presence of a copper-containing catalyst in a reaction solvent having an ionization potential of from 8.0 to 9.0 eV.

(2) the method for producing arylamine according to the aforementioned item (1) wherein the reaction solvent is selected from terpenes having at least one double bond in the molecule.

(3) the method for producing arylamine according to the aforementioned item (1) wherein the reaction solvent is selected from terpinenes, terpinolenes and phellandrenes.

(4) the method for producing arylamine according to the aforementioned item (1) wherein the reaction is carried out in the presence of a cyclic nitrogen-containing compound.

(5) the method for producing arylamine according to the aforementioned item (4) wherein the cyclic nitrogen-containing compound is a compound represented by the following general formula (1):

$$(1)$$

wherein A represents a nitrogen atom or an N-oxide (N→O), Q is not present or Q represents an atomic group which forms, together with the ring containing A, a five-membered or six-membered ring, R1 and R2, which may be the same as or different from each other, each represents a hydrogen atom, an alkyl group, a hydroxy group, a hydroxyalkyl group, a carboxyl group, a carboxyalkyl group, a formyl group, an acyl group, a pyridyl group or a quinolyl group, and each of a and b is an integer of from 1 to 3, with the proviso that a plurality of R1 or R2 may be the same as or different from one another.

(6) the method for producing arylamine according to the aforementioned item (4) wherein the cyclic nitrogen-containing compound is picolinic acid or quinolinic acid.

(7) the method for producing arylamine according to the aforementioned item (4) wherein the cyclic nitrogen-containing compound is a compound represented by the following general formula (2):

$$(2)$$

wherein Q, A, R1, R2, a and b have the same significance as Q, A, R1, R2, a and b above.

(8) the method for producing arylamine according to the aforementioned item (4) wherein the cyclic nitrogen-containing compound is 2,2'-bipyridyl or 1,10-phenanthroline.

(9) the method for producing arylamine according to the aforementioned item (1) wherein the copper-containing catalyst is a ligand-linked copper salt represented by the following general formula (3):

$$[CuL_1]Xm \cdot nH_2O \qquad (3)$$

wherein Cu represents a monovalent or divalent copper element, L represents a compound represented by the following general formula (4), l is an integer of from 1 to 6, X represents OH, Cl, Br, I, $NO_2$, $NO_3$, $SO_4$, $ClO_4$, $BF_4$, $BF_6$, $PF_6$, SCN, NCS or $S_2O_8$, m is a natural number of from 0 to 2 and n is a natural number of from 0 to 10,

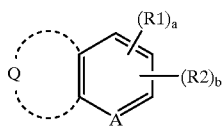

(4)

wherein Q, A, R1, R2, a and b have the same significance as Q, A, R1, R2, a and b above.

(10) the method for producing arylamine according to the aforementioned item (9) wherein the ligand-linked copper salt is selected from picolinic acid copper salts and quinolinic acid copper salts.

(11) the method for producing arylamine according to the aforementioned item (1) wherein the copper-containing catalyst is a ligand-linked copper salt represented by the following general formula (5):

$$[CuL_1]Xm.nH_2O \qquad (5)$$

wherein L represents a compound represented by the following general formula (6), and Cu, X, l, m and n have the same significance as Cu, X, l, m and n above,

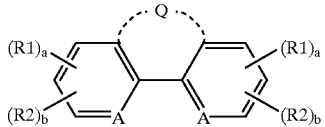

(6)

wherein Q, A, R1, R2, a and b have the same significance as Q, A, R1, R2, a and b above.

(12) the method for producing arylamine according to the aforementioned item (11) wherein the ligand-linked copper salt is selected from 2,2'-bipyridyl copper salts.

Other objects and advantages of the present invention will be made apparent as the description progresses.

DETAILED DESCRIPTION OF THE INVENTION

According to the present invention, a high purity compound of interest is obtained in a high yield by the use of a copper-containing catalyst in a reaction solvent having an ionization potential of from 8.0 to 9.0 eV, preferably from 8.5 to 9.0 eV, in carrying out Ullmann condensation reaction for the production of an arylamine, in particular a group of triarylamines or diarylamines which are useful as raw materials for electronic materials use or as intermediates thereof.

It was found that such an effect becomes more remarkable particularly when terpenes, in particular terpenes having at least one double bond in the molecule are used as the reaction solvent.

Also, according to the present invention, the reaction can be completed within a short period of time, and a compound of interest therefore can be obtained with a high purity and at a low cost, by the use of a copper-containing catalyst and a cyclic nitrogen-containing compound as a co-catalyst in a reaction solvent having an ionization potential of from 8.0 to 9.0 eV, preferably from 8.5 to 9.0 eV, in carrying out Ullmann condensation reaction for the production of an arylamine, in particular a group of triarylamines or diarylamines which are useful as raw materials for electronic materials use or as intermediates thereof.

In addition, according to the present invention, the reaction can be completed within a short period of time and a high purity compound of interest can therefore be obtained within a short period of time and in a high yield, by carrying out the Ullmann condensation reaction in a reaction solvent having an ionization potential of from 8.0 to 9.0 eV, preferably from 8.5 to 9.0 eV, and in the presence of a ligand-linked copper salt represented by the aforementioned general formula (3) or (5), for the production of an arylamine, in particular a group of triarylamines or diarylamines which are useful as raw materials for electronic materials use or as intermediates thereof.

It was found that such an effect becomes more remarkable particularly when terpenes are used as the reaction solvent.

With regard to the copper-containing catalyst to be used in the present invention, any catalyst usually used in the Ullmann condensation reaction can be used with no particular limitation, and its illustrative examples include copper powder, cuprous chloride, cupric chloride, cuprous bromide, cupric bromide, copper iodide, cuprous oxide, cupric oxide, copper acetate, copper sulfate, copper nitrate, copper carbonate, cupric acetate, cupric hydroxide and the like, of which cupric bromide, copper iodide and copper sulfate are preferred. According to the production method of the present invention, the copper-containing catalyst is used in an amount of preferably from 0.001 to 0.1 mole, more preferably from 0.005 to 0.05 mole, based on 1 mole of the aromatic halide.

The cyclic nitrogen-containing compound to be used as a co-catalyst in the present invention is at least one of the compounds represented by the aforementioned general formula (1) or (2).

Furan ring, thiophene ring, pyrrole ring, pyrazole ring, imidazole ring and the like can be exemplified as the five-membered ring which is formed by the Q-containing constituting moiety in the aforementioned general formula (1) or (2), and benzene ring, cyclohexane ring, pyridine ring and the like as the six-membered ring.

In the aforementioned general formula (1) or (2), R1 and R2 may be the same as or different from each other and each represents a hydrogen atom, an alkyl group, a hydroxy group, a hydroxyalkyl group, a carboxyl group, a carboxyalkyl group, a formyl group, an acyl group, a pyridyl group or a quinolyl group.

Illustrative examples of the compounds represented by the general formula (1) or (2) include γ-picoline, 2,4-lutidine, 2,4,6-collidine, picolinic acid, quinolinic acid, 2-pyridylacetic acid, pyridine-2-aldehyde, 2-pyridinemethanol, 2-pyridineethanol, 2-hydroxypyridine, quinoline, quinaldine, 4-methylquinoline, 8-quinolinol, quinaldic acid, 2,2'-bipyridyl, 1,10-phenanthroline and the like, of which picolinic acid, quinolinic acid, 2,2'-bipyridyl and 1,10-phenanthroline are particularly effective.

The use of a cyclic nitrogen-containing compound as a co-catalyst has an advantage in that the reaction can be completed within a short period of time by selecting the most suitable co-catalyst for the materials to be used, and such a compound is generally used in an amount of preferably from 0.1 to 6.0 moles, more preferably from 0.5 to 2.0 moles, based on 1 mole of the copper-containing catalyst.

In that case, the reaction is carried out generally at a temperature of from 190 to 210° C. for a period of from 1 to 12 hours, preferably 1 to 4 hours, more preferably at a temperature of from 200 to 210° C. for a period of from 1.5 to 3 hours, though these conditions vary depending on the materials and co-catalyst to be used. In this connection, in order to produce a high purity arylamine by preventing formation of by-products, it is desirable to carry out the reaction in an atmosphere of an inert gas, particularly in a stream of nitrogen.

The ligand-linked copper salt represented by the general formula (3) or (5) to be used as a catalyst in the present invention is synthesized from a copper salt and an organic ligand compound represented by the aforementioned general formula (4) or (6).

Illustrative examples of the copper salt to be used in the present invention include cuprous chloride, cupric chloride, cuprous bromide, cupric bromide, copper iodide, cuprous oxide, cupric oxide, cupric hydroxide, copper carbonate, copper acetate, copper sulfate, copper nitrate and the like.

In the organic ligand compound represented by the aforementioned general formula (4) or (6) to be used in the present invention, examples of the five-membered ring and six-membered ring which are formed by the Q-containing constituting moiety include the same five-membered rings and six-membered rings which are formed by the Q-containing constituting moiety in the aforementioned general formula (1) or (2).

Examples of R1 in the aforementioned general formula (4) or (6) include the same groups of R1 in the aforementioned general formula (1) or (2).

Examples of R2 in the aforementioned general formula (4) or (6) include the same groups of R2 in the aforementioned general formula (1) or (2).

Illustrative examples of the compound represented by the aforementioned general formula (4) or (6) include the same illustrative compounds represented by the aforementioned general formula (1) or (2).

The ligand-linked copper salt is used by synthesizing it in accordance with a known method (for example, the method disclosed in *J. Chem. Soc.*, 1969 A, 2219; *Aust. J. Chem.*, 17, 219 (1964); *Z. Anorg. Chem.*, 227, 273 (1986); *J. Inorg. Nucl. Chem.*, 9, 211 (1959) or the like). That is, it can be synthesized for example by a method in which the aforementioned copper salt and organic ligand compound are separately dissolved in water or an alcohol and then mixed, and the thus precipitated crystals are collected by filtration and dried or by a method in which a mixed solution of the copper salt and organic ligand compound is stirred under heating and then dried by its concentration to dryness. In general, the organic ligand compound is used in an amount of 1, 2 or 3 equivalents based on the copper salt.

Preferred examples of the aforementioned ligand-linked copper salt which can be used in the present invention include 2,2'-bipyridylcopper(II) nitrate trihydrate, 2,2'-bipyridylcopper(II) sulfate dihydrate, bis(2,2'-bipyridyl)copper(II) chloride hexahydrate, bis(2,2'-bipyridyl)copper nitrate monohydrate, bis(pyridine-2-carboxylic acid)copper(II) chloride hexahydrate and the like.

When a ligand-linked copper salt is commercially available such as 8-quinolinolcopper or the like, its direct use without further synthesis may be effective, but 2,2'-bipyridylcopper, copper picolinate, copper quinolinate or the like is particularly effective.

The use of such a ligand-linked copper salt as the copper-containing catalyst has an advantage in that the reaction can be completed within a short period of time by selecting the most suitable catalyst for the materials to be used, and it is used in an amount of generally from 0.001 to 0.1 mole, preferably from 0.005 to 0.02 mole, based on 1 mole of the aromatic halide.

In that case, the reaction is carried out generally at a temperature of from 190 to 210° C. for a period of from 4 to 10 hours, though these conditions vary depending on the materials and ligand-linked copper salt to be used.

With regard to the aforementioned reaction solvent which can be used in the present invention, any solvent having an ionization potential of from 8.0 to 9.0 eV can be used, but terpenes, in particular terpens having at least one double bond in the molecule are particularly desirable. Terpenes are compounds which are broadly used generally as materials of medicaments and perfumes.

Illustrative examples of terpenes include ocimene, myrcene, α-terpinen, β-terpinen, γ-terpinen, terpinolene, (+)-α-phellandrene, (−)-β-phellandrene, (−)-1-p-menthene, (+)-3-p-memthene, dipentene, (+)-limonene, (+)-sabinene, (+)-α-pinene, (+)-β-pinene and the like monoterpene compounds and (−)-β-cadinene, (−)-β-caryophyllene, (−)-β-santalene, (−)-α-cedrene, (+)-β-selinene, (−)-β-bisabolene, α-humulene and the like sesquiterpene compounds, of which terpinens, terpinolenes and phellandrenes are particularly effective.

Also included are geraniol, (+)-citronellol, nellol, (+)-linalool, cis-citral, trans-citral, (+)-citronellal, (+)-isomenthol, (+)-cis-carveol, (+)-trans-carveol, (−)-carvomenthol, (+)-dihydrocarveol, (+)-α-terpineol, trans-β-terpineol, γ-terpineol, (+)-1-p-menthen-4-ol, (−)-menthol, trans-1,4-terpin, cic-1,8-terpin, (+)-trans-sobrerol, (−)-isopulegone, (+)-isomenthone, carvenone, (+)-carvotanacetone, (−)-carvomenthone, (+)-carvone, (−)-dihydrocarvone, (−)-piperitone, (+)-pulegone, (−)-menthone, diosphenol, α-thujone and the like monoterpene compounds and farnesol, (+)-nerolidol and the like sesquiterpene compounds.

The term "ionization potential" as used herein means a value which represents the first ionization potential by photoelectron spectrum, and it can be measured for example by a photoelectron spectrometry in which it is calculated from the kinetic energy distribution of photoelectrons generated by photo-ionization or by a vacuum ultraviolet ray absorption method in which it is calculated from the measurement of the series end of emission or adsorption spectrum in the vacuum ultraviolet region.

When a reaction solvent having an ionization potential of smaller than 8.0 eV is used, the reaction solvent, materials and formed product will react with one another in some cases, and when a reaction solvent having an ionization potential of larger than 9.0 eV is used, progress in the reaction becomes slow and purification of the formed product becomes difficult because of the increased by-production of impurities, so that the desired end cannot be achieved.

According to the present invention, the aforementioned reaction solvent is used in an amount of generally from 250 to 450 ml based on 1 mol of the material aromatic amine.

As the arylamine to be produced by the present invention, the triarylamine or diarylamine represented by the following general formula (I), (II) or (III) can be cited.

(I)

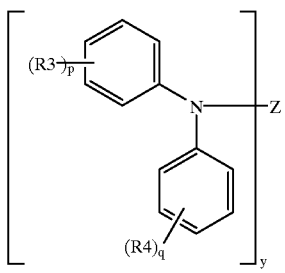

(II)

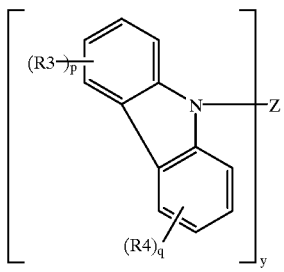

(III)

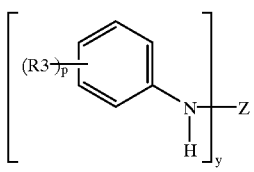

In the above formulae, R3 and R4 each represents a substituent group having a Hammett's σm value of from −0.34 to 0.71 or a substituent group having a σp value of from −0.84 to 0.73, wherein a plurality of R3 or R4 may be the same as or different from one another or two groups of a plurality of R3 or R4 may be linked to each other to form a ring, y is an integer of 1 to 3, each of p and q is an integer of from 1 to 4, and Z represents a y-valency group which forms a linking arm at an optional position of the aromatic ring of compounds represented by the following general formulae.

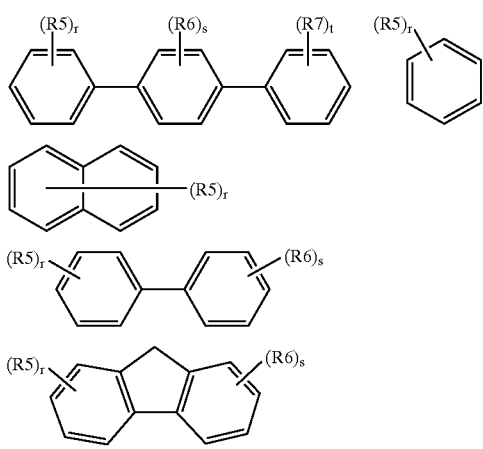

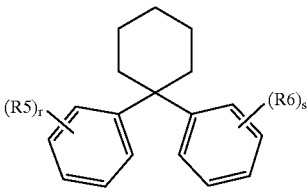

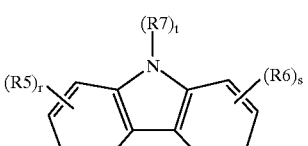

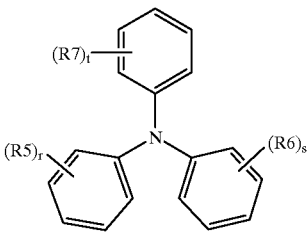

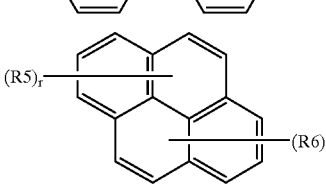

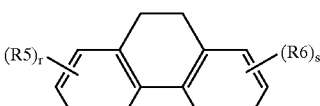

In the above formulae, each of R5, R6 and R7 independently represents a substituent group having a Hammett's σm value of from −0.15 to 0.43 or a substituent group having a σp value of from −0.32 to 0.54, which may be linked to any position of the aromatic ring, and each of r, s and t is an integer of from 1 to 5.

Cyclohexyl ring, benzene ring and the like can be exemplified as the ring formed by the mutual linking of two groups of a plurality of R3 or R4.

Illustrative examples of the substituent group having a Hammett's σm value of from −0.34 to 0.71 include methyl, t-butyl and the like alkyl groups, cyclopentyl, cyclohexyl and the like cycloalkyl groups, vinyl and the like alkenyl groups, phenyl, naphthyl and the like aryl groups, methoxy, ethoxy and the like alkoxy groups, amino, dimethylamino and the like amino groups, nitro group and chlorine, bromine and the like halogen atoms, and illustrative examples of the substituent group having a σp value of from −0.84 to 0.73 include methyl, t-butyl and the like alkyl groups, vinyl and the like alkenyl groups, methoxy, ethoxy and the like alkoxy groups, amino, dimethylamino and the like amino groups, nitro group and chlorine, bromine and the like halogen atoms.

Also, illustrative examples of the substituent group having a Hammett's σm value of from −0.15 to 0.43 include methyl, t-butyl and the like alkyl groups, cyclopentyl, cyclohexyl and the like cycloalkyl groups, phenyl, naphthyl and the like aryl groups and methoxy, ethoxy and the like alkoxy groups, and illustrative examples of the substituent group having a op value of from −0.32 to 0.54 include methyl, t-butyl and the like alkyl groups, cyclopentyl, cyclohexyl and the like cycloalkyl groups, phenyl, naphthyl and the like aryl groups, methoxy, ethoxy and the like alkoxy groups and chlorine and the like halogen atoms.

The following can be cited as illustrative examples of the compound represented by the general formula (I), (II) or (III).

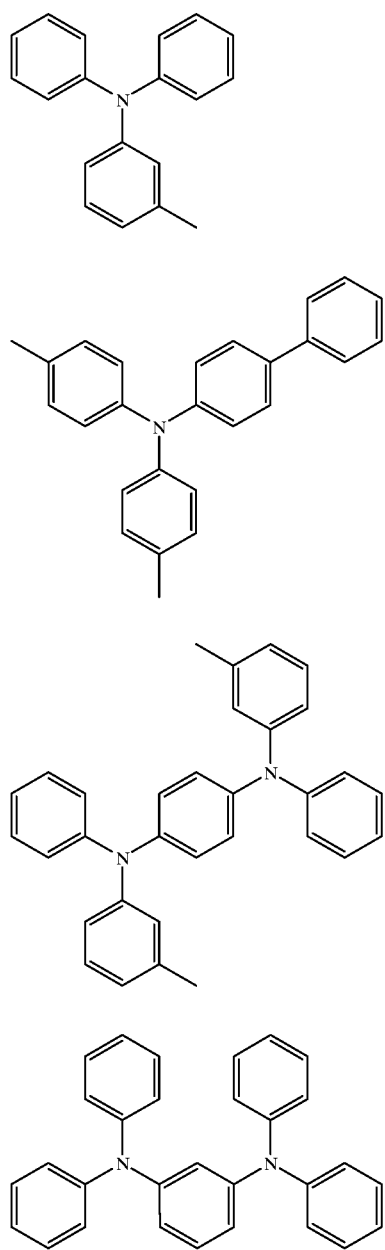

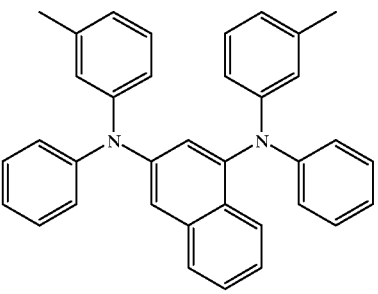

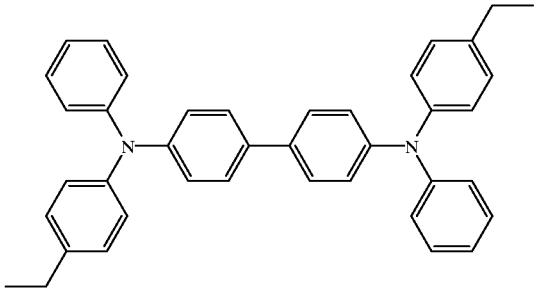

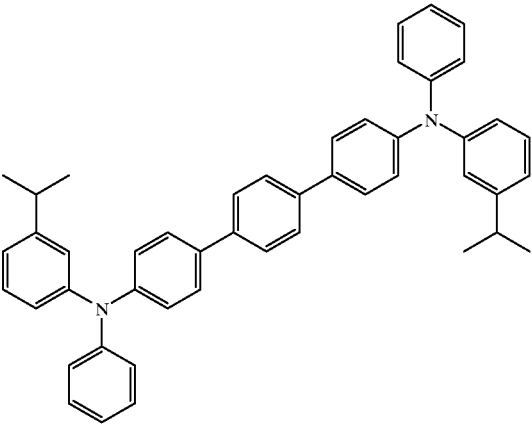

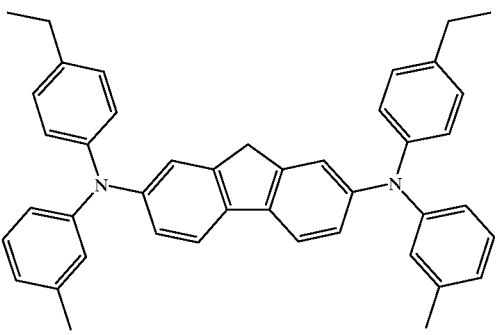

(I-9)
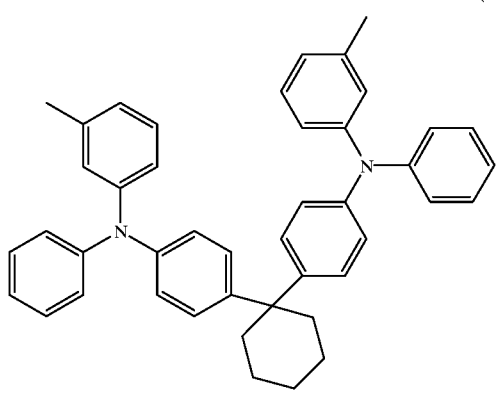
(I-13)
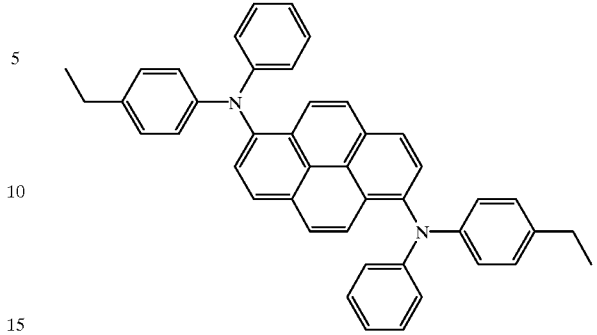
(I-10)
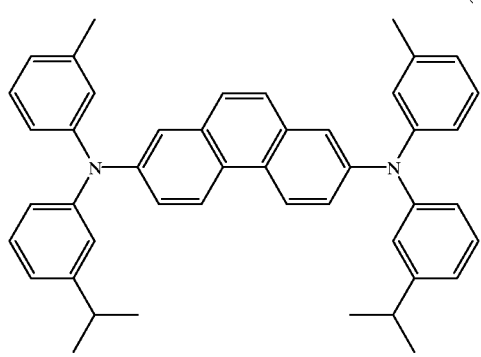
(I-14)
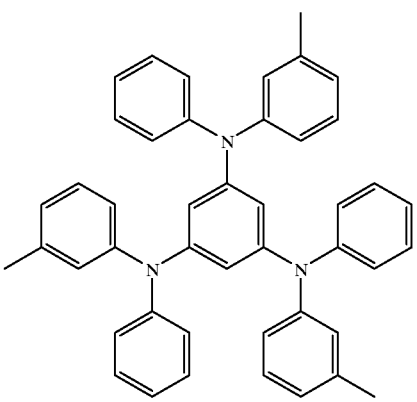
(I-11)
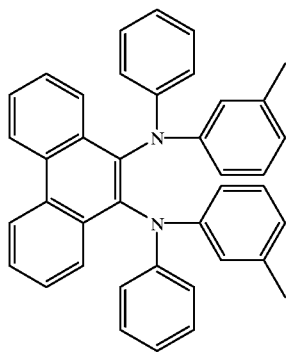
(I-15)
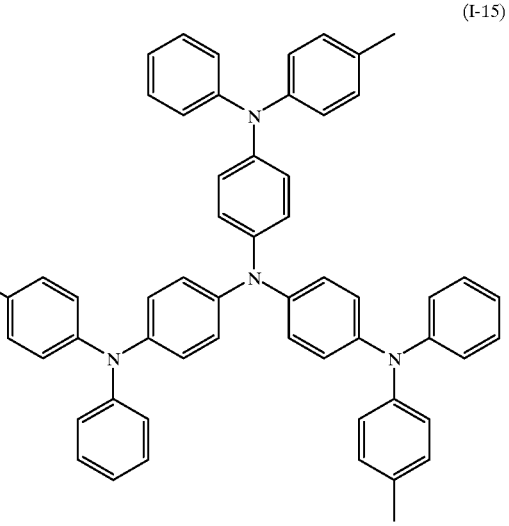
(I-12)
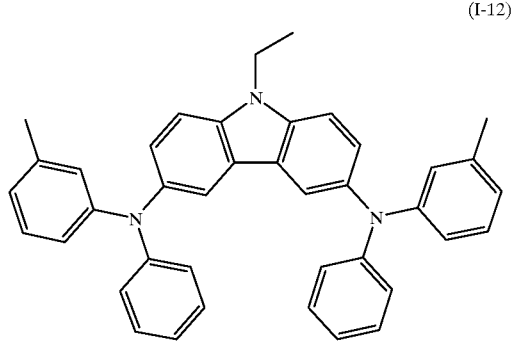
(I-16)
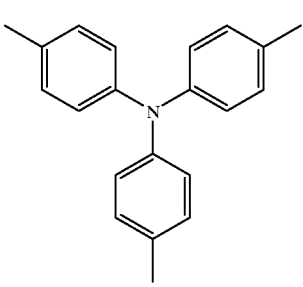

(I-17)
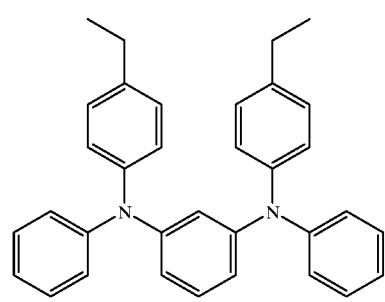
(I-18)
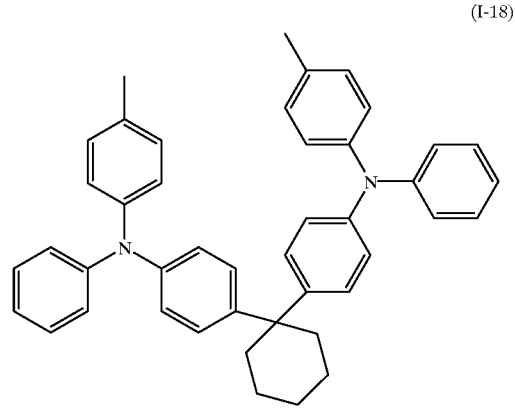
(I-19)
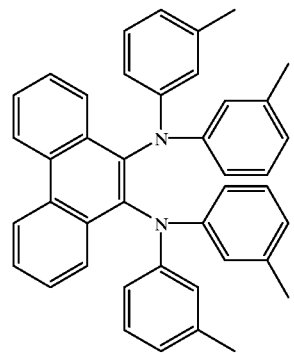
(I-20)
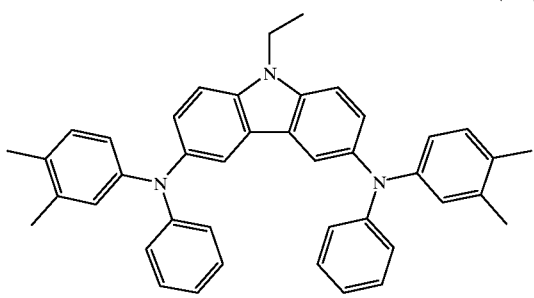
(I-21)
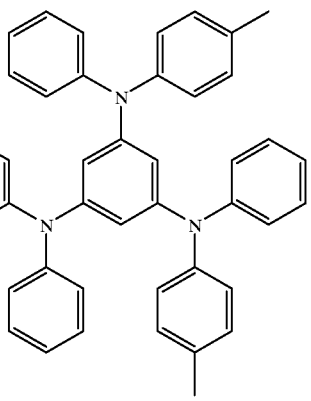
(II-1)
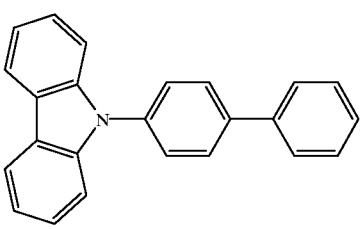
(II-2)
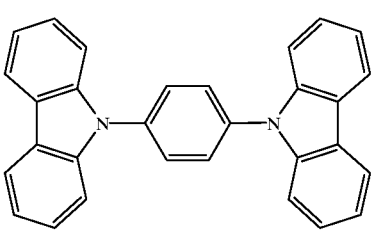
(II-3)
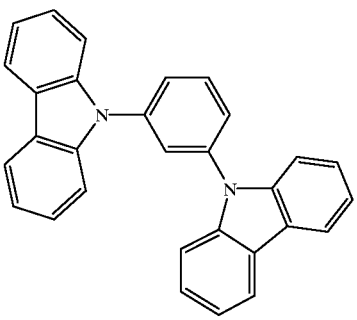
(II-4)
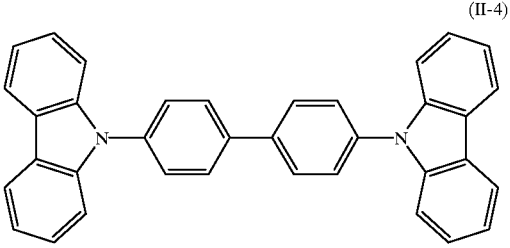

-continued
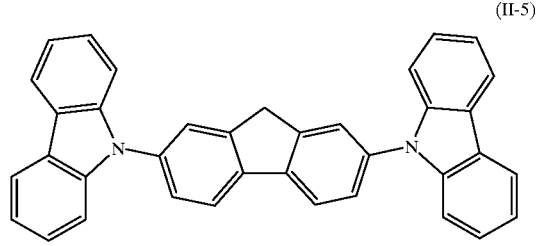
(II-5)
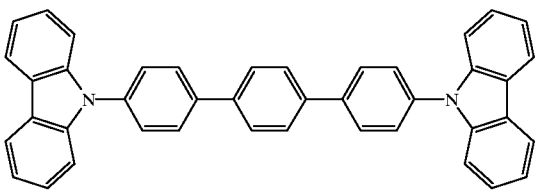
(II-6)
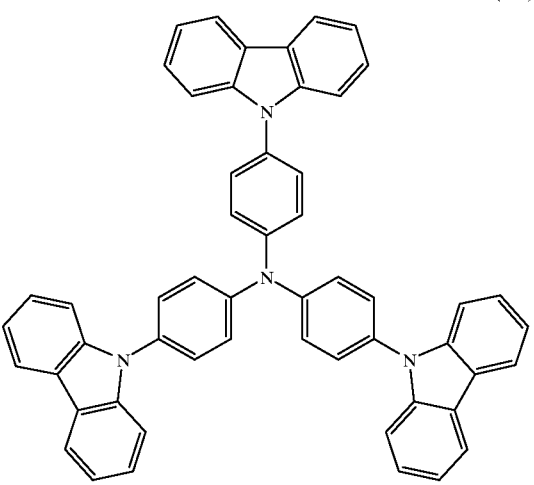
(II-7)
(III-1)
(III-2)
-continued
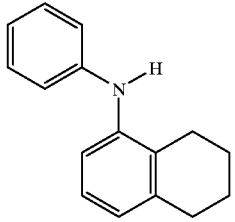
(III-3)
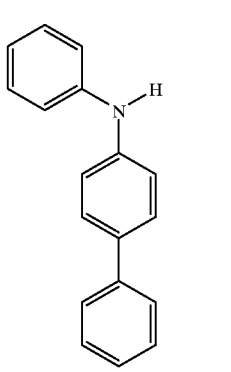
(III-4)
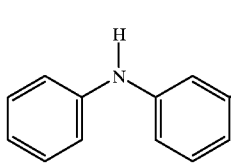
(III-5)
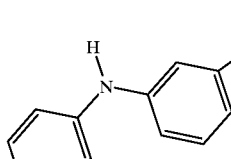
(III-6)
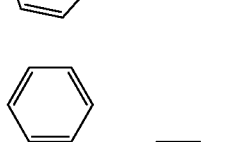
(III-7)
(III-8)

-continued (III-9)

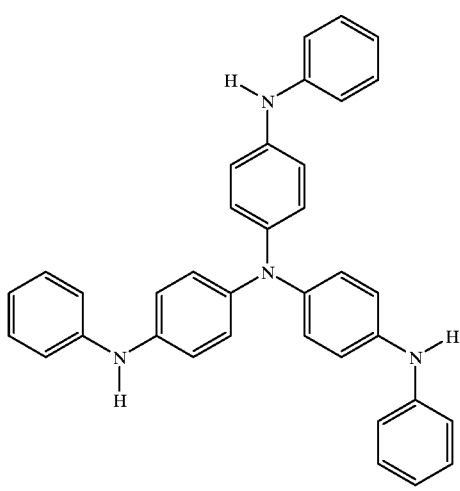

Examples of the aromatic amine to be used for the production of the arylamine, in particular the aforementioned triarylamine or diarylamine, of the present invention include those amines in which Z of the compounds represented by the aforementioned general formula (I), (II) or (III) is replaced by hydrogen atom.

Also, a halide, generally iodide, of a compound which corresponds to Z in the aforementioned general formula (I), (II) or (III) is used as the aromatic halide, and the halide is used in an amount of generally from 0.3 to 4.0 equivalents, preferably from 0.9 to 2.0 equivalents, based on 1 equivalent of the aromatic amine.

Examples of the present invention are given below by way of illustration and not by way of limitation. In this connection, the purity of compounds was evaluated by means of a high performance liquid chromatography (to be referred to as "HPLC" hereinafter).

EXAMPLE 1
<Synthesis of tri(4-methylphenyl)amine (I-16)>

A mixture consisting of 70.0 g (0.36 mol) of di(4-methylphenyl)amine, 100.0 g (0.46 mol) of p-iodotoluene, 70.0 g (0.50 mol) of potassium carbonate, 5.0 g (0.02 mol) of copper sulfate pentahydrate and 150 ml of terpinolene (ionization potential, 8.98) was allowed to undergo 6 hours of the reaction at 200 to 210° C. in a stream of nitrogen. After completion of the reaction, 150 ml of toluene and 150 ml of water were added to the reaction mixture to carry out separation of layers. After evaporation of toluene by concentration under a reduced pressure, crystallization was effected by adding 355 ml of ethyl acetate and 2,483 ml of methanol to the resulting residue, thereby obtaining 192.9 g (94.5% in yield) of the compound of interest (I-16) as white crude crystals. Its melting point was found to be 116 to 117° C. and the purity measured by HPLC (column, YMC-A-312; elution solution, methanol/tetrahydrofuran (to be referred to as "THF" hereinafter)=99/1 (v/v); detection, UV at 300 nm; flow rate, 1.0 ml/min) was found to be 99.5%.

Elemental analysis (for $C_{21}H_{21}N$) Calcd. (%): C, 87.72 H, 7.36 Found (%): C, 87.75 H, 7.34

EXAMPLE 2
<Synthesis of N,N,N',N'-tetra(3-methylphenyl)-9,10-diaminophenthrene (I-19)>

A mixture consisting of 66.0 g (0.17 mol) of 9,10-di(3-methylanilino)phenanthrene, 110.7 g (0.51 mol) of m-iodotoluene, 93.6 g (0.68 mol) of potassium carbonate, 1.8 g (0.008 mol) of cupric bromide and 74 ml of α-terpinene was allowed to undergo 10 hours of the reaction at 200 to 210° C. in a stream of nitrogen. After completion of the reaction, the reaction solvent was evaporated by concentration under a reduced pressure, 45 ml of toluene, 666 ml of ethyl acetate and 222 ml of water were added to the resulting residue to carry out separation of layers and then crystallization was effected by adding 708 ml of methanol, thereby obtaining 94.1 g (97.3% in yield) of the compound of interest (I-19) as light yellow crude crystals. Its melting point was found to be 223 to 224° C. and the purity measured by HPLC (column, YMC-A-312; elution solution, methanol/THF=99/1 (v/v); detection, UV at 254 nm; flow rate, 1.0 ml/min) was found to be 99.6%.

Elemental analysis (for $C_{42}H_{36}N_2$) Calcd. (%): C, 88.69 H, 6.38 Found (%): C, 88.72 H, 6.36

EXAMPLES 3 AND 4 AND COMPARATIVE EXAMPLES 1 AND 2

The compound of interest (I-19) was synthesized by repeating the reaction of Example 2, except that the solvents shown in the following Table 1 were used in stead of α-terpinene used in Example 2. Purity of the product was evaluated by HPLC in the same manner except that the reaction solvent was changed. The results are shown in Table 1.

TABLE 1

| Reaction solvent | | Ionization potential (eV) | HPLC purity (%) | Yield (%) |
|---|---|---|---|---|
| Kind | Amount | | | |
| Ex. 2 | α-terpinene | 74 ml | 8.63 | 99.6 | 97.3 |
| Ex. 3 | γ-terpinene | " | 8.99 | 99.6 | 97.0 |
| Ex. 4 | terpinolene | " | 8.98 | 99.5 | 97.7 |
| Comp. Ex. 1 | n-decane | " | 10.19 | 98.7 | 87.3 |
| Comp. Ex. 2 | nitrobenzene | " | 10.26 | 98.6 | 86.0 |

As is evident from the results shown in Table 1, in comparison with the saturated aliphatic hydrocarbon compound or aromatic compound conventionally used as the reaction solvent, the compound of interest having more higher purity was obtained when terpene compounds were used as the reaction solvent.

EXAMPLE 5
<Synthesis of 3-methyltriphenylamine (I-1)>

A mixture consisting of 20.3 g (0.12 mol) of diphenylamine, 26.0 g (0.12 mol) of m-iodotoluene, 32.6 g (0.24 mol) of potassium carbonate, 0.27 g (0.001 mol) of copper sulfate pentahydrate, 0.12 g of picolinic acid and 32 ml of terpinolene (ionization potential, 8.98 eV) was allowed to undergo 1.5 hours of the reaction at 200 to 210° C. in a stream of nitrogen. After completion of the reaction, 66 ml of toluene and 66 ml of water were added to the reaction mixture to carry out separation of layers and then toluene was concentrated under a reduced pressure. Thereafter, crystallization was effected by adding 39 ml of ethyl acetate and 243 ml of methanol to the resulting residue, thereby obtaining 29.9 g (96.1% in yield) of the compound of interest (I-1) as light yellow crude crystals. Its melting point was found to be 69 to 70° C. and its purity measured by HPLC (column, YMC-A-312; elution solution, methanol/THF=99/1 (v/v); detection, UV at 300 nm; flow rate, 1.0 ml/min) was found to be 99.6%.

Elemental analysis (for $C_{19}H_{17}N$) Calcd. (%): C, 87.99 H, 6.61 Found (%): C, 88.02 H, 6.59

EXAMPLE 6
<Synthesis of N,N'-diphenyl-N,N'-di(3-methylphenyl)-1,4-phenylenediamine (I-3)>

A mixture consisting of 33.8 g (0.13 mol) of N,N'-diphenyl-p-phenylenediamine, 58.9 g (0.27 mol) of m-iodotoluene, 74.6 g (0.54 mol) of potassium carbonate, 0.84 g (0.003 mol) of copper sulfate pentahydrate, 0.42 g (0.003 mol) of picolinic acid and 40 ml of terpinolene was allowed to undergo 3 hours of the reaction at 200 to 210° C. in a stream of nitrogen. After completion of the reaction, 66 ml of toluene and 66 ml of water were added to the reaction mixture to carry out separation of layers and then toluene was concentrated under a reduced pressure. Thereafter, crystallization was effected by adding 39 ml of ethyl acetate and 253 ml of isopropyl alcohol (to be referred to as "IPA" hereinafter) to the resulting residue, thereby obtaining 50.2 g (94.9% in yield) of the compound of interest (I-3) as light yellow crude crystals. Its melting point was found to be 170 to 171° C. and its purity measured by HPLC (column, YMC-A-002; elution solution, hexane/THF (95/5); detection, UV at 310 nm; flow rate, 1.1 ml/min) was found to be 99.3%.

Elemental analysis (for $C_{32}H_{28}N_2$) Calcd. (%): C, 87.23 H, 6.41 Found (%): C, 87.28 H, 6.43

COMPARATIVE EXAMPLES 3 TO 5

The compound of interest (I-3) was synthesized by carrying out the reaction of Example 6 using terpinolene used in Example 6 or the solvents shown in the following Table 2. The purity and yield were evaluated by HPLC in the same manner, except that the reaction solvent was changed and the reaction was carried out in the presence or absence of the co-catalyst. The results are shown in Table 2.

EXAMPLE 8
<Synthesis of N,N,N',N'-tetraphenyl-1,3-phenylenediamine (I-4)>

A mixture consisting of 24.9 g (0.23 mol) of m-phenylenediamine, 129.0 g (0.93 mol) of potassium carbonate, 6.65 g (0.012 mol) of bis(2,2'-bipyridyl)copper (II) chloride hexahydrate and 98 ml of terpinolene was stirred at 190 to 195° C. in a stream of nitrogen, 179.5 g (0.88 mol) of iodobenzene was added dropwise to the reaction mixture spending 1 hour and then the resulting mixture was allowed to undergo additional 4 hours of the reaction. After completion of the reaction, 210 ml of toluene and 210 ml of water were added to the reaction mixture to carry out separation of layers and then toluene was concentrated under a reduced pressure. Thereafter, crystallization was effected by adding 160 ml of ethyl acetate and 980 ml of IPA to the resulting residue, thereby obtaining 89.5 g (94.3% in yield) of the compound of interest (I-4) as light yellow crude crystals. Its melting point was found to be 131 to 132° C. and its purity measured by HPLC (column, super-ODS; elution solution, methanol; detection, UV at 254 nm; flow rate, 0.6 ml/min) was found to be 99.5%.

Elemental analysis (for $C_{30}H_{24}N_2$) Calcd. (%): C, 87.34 H, 5.86 Found (%): C, 87.38 H, 5.88

EXAMPLE 9
<Synthesis of N,N'-di(3-methylphenyl)-N,N'-diphenyl-9,10-diaminophenanthrene (I-11)>

A mixture consisting of 62.0 g (0.17 mol) of 9,10-dianilinophenanthrene, 110.7 g (0.51 mol) of m-iodotoluene, 93.6 g (0.68 mol) of potassium carbonate, 4.44 g (0.008 mol) of bis(2,2'-bipyridyl)copper(II) chloride hexahydrate and 50 ml of terpinolene was allowed to undergo 6 hours of the reaction at 200 to 210° C. in a stream of nitrogen. After

TABLE 2

| | Reaction solvent | | IP* | Co-catalyst | | Reaction time | Purity by HPLC | Yield |
|---|---|---|---|---|---|---|---|---|
| Example | Kind | Amount | (eV) | Kind | Amount | (h) | (%) | (%) |
| Ex. 6 | terpinolene | 32 ml | 8.98 | PA* | 0.002 mol | 3 | 99.4 | 95.0 |
| Comp. 3 | terpinolene | 32 ml | 8.98 | PA | 0 mol | 15 | 99.4 | 93.7 |
| Comp. 4 | n-decane | 32 ml | 10.19 | PA | 0.002 mol | 10 | 98.7 | 88.0 |
| Comp. 5 | nitrobenzene | 32 ml | 10.26 | PA | 0.002 mol | 8 | 98.5 | 85.7 |

IP: ionization potential
PA: picolinic acid

As is evident from the results shown in Table 2, in comparison with the saturated aliphatic hydrocarbon compound and aromatic compound conventionally used as the reaction solvent, the reaction was considerably accelerated by the addition of the cyclic nitrogen-containing compound, and the compound of interest having more higher purity was obtained when the reaction solvent having an ionization potential of 8.0 to 9.0 eV was used.

EXAMPLE 7
<Synthesis of bis(2,2'-bipyridyl)copper(II) chloride hexahydrate>

A 17.7 g (0.1 mol) portion of copper(II) chloride dihydrate was dissolved in 800 ml of water under heating, to which was then added 31.2 g (0.2 mol) of 2,2'-bipyridyl which has been dissolved in 300 ml of ethanol. The resulting solution was cooled, and the thus precipitated crystals were collected by filtration, washed with ethanol and then dried under vacuum, thereby obtaining 52.7 g (94.9% in yield) of the compound of interest as deep blue crystals.

completion of the reaction, 45 ml of toluene, 1,666 ml of ethyl acetate and 222 ml of water were added to the reaction mixture to carry out separation of layers and then crystallization was effected by adding 708 ml of methanol, thereby obtaining 89.6 g (96.8% in yield) of the compound of interest (I-11) as light yellow crude crystals. Its melting point was found to be 231 to 232° C. and its purity measured by HPLC (column, YMC-A-312; elution solution, methanol/THF (99/1); detection, UV at 254 nm; flow rate, 1.0 ml/min) was found to be 99.4%.

Elemental analysis (for $C_{40}H_{36}N_2$) Calcd. (%): C, 88.19 H, 6.66 Found (%): C, 88.23 H, 6.633

COMPARATIVE EXAMPLES 6 TO 8

The compound of interest (I-11) was synthesized by carrying out the same reaction of Example 9 using terpinolene used in Example 9 or the solvents shown in the following Table 3. Purity of the compound was evaluated by HPLC in the same manner, except that the reaction solvent and copper-containing catalyst were varied. The results are shown in Table 3.

TABLE 3

| Example | Reaction solvent Kind | Amount | IP* (eV) | Copper-containing catalyst Kind | Amount | Reaction time (h) | Purity by HPLC (%) | Yield (%) |
|---|---|---|---|---|---|---|---|---|
| Ex. 9 | terpinolene | 50 ml | 8.98 | BCo* | 0.008 mol | 6 | 99.4 | 96.8 |
| Comp. 6 | terpinolene | 50 ml | 8.98 | CoS* | 0.008 mol | 20 | 99.4 | 96.7 |
| Comp. 7 | n-decane | 50 ml | 10.19 | BCo | 0.008 mol | 15 | 98.2 | 89.0 |
| Comp. 8 | nitrobenzene | 50 ml | 10.26 | BCo | 0.008 mol | 12 | 98.0 | 87.3 |

IP: ionization potential
BCo: bis(2,2'-bipyridyl)copper(II) chloride hexahydrate
COS: copper sulfate As is evident from the results shown in Table 3, in comparison with the saturated aliphatic hydrocarbon compound and aromatic compound conventionally used as the reaction solvent, the reaction was considerably accelerated by the use of a ligand-linked copper salt as the copper-containing catalyst, and the compound of interest having more higher purity was obtained when the reaction solvent having an ionization potential of 8.0 to 9.0 eV was used.

Thus, as has been described in the foregoing, according to the arylamine production method of the present invention, an arylamine, in particular a triarylamine or diarylamine, useful as a raw material for use in electronic materials or as an intermediate thereof can be produced with a high purity and at a low cost (high yield within a short period of reaction time) or in a high yield, so that it has markedly high practical value.

While the invention has been described in detail and with reference to specific embodiments thereof, it will be apparent to one skilled in the art that various changes and modifications can be made therein without departing from the spirit and scope thereof.

What is claimed is:

1. A method for producing arylamine which comprises allowing an aromatic amine to react with an aromatic halide in the presence of a copper-containing catalyst in a reaction solvent having an ionization potential of from 8.0 to 9.0 eV.

2. The method for producing arylamine according to claim 1 wherein the reaction solvent is selected from terpenes having at least one double bond in the molecule.

3. The method for producing arylamine according to claim 1 wherein the reaction solvent is selected from terpinenes, terpinolenes and phellandrenes.

4. The method for producing arylamine according to claim 1 wherein the reaction is carried out in the presence of a cyclic nitrogen-containing compound.

5. The method for producing arylamine according to claim 4 wherein the cyclic nitrogen-containing compound is a compound represented by the following general formula (1):

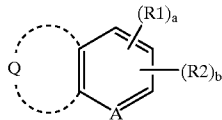

wherein A represents a nitrogen atom or an N-oxide (N→O), Q is not present or Q represents an atomic group which forms, together with the ring containing A, a five-membered or six-membered ring, R1 and R2, which may be the same as or different from each other, each represents a hydrogen atom, an alkyl group, a hydroxy group, a hydroxyalkyl group, a carboxyl group, a carboxyalkyl group, a formyl group, an acyl group, a pyridyl group or a quinolyl group, and each of a and b is an integer of from 1 to 3, with the proviso that a plurality of R1 and R2 may be the same as or different from one another.

6. The method for producing arylamine according to claim 5 wherein the cyclic nitrogen-containing compound is picolinic acid or quinolinic acid.

7. The method for producing arylamine according to claim 4 wherein the cyclic nitrogen-containing compound is a compound represented by the following general formula (2):

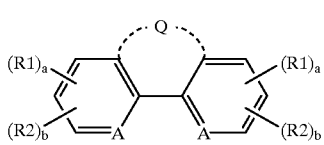

wherein A represents a nitrogen atom or an N-oxide (N→O), Q represents an atomic group which is necessary for the Q-containing constituting moiety to form a five-membered or six-membered ring, R1 and R2, which may be the same as or different from each other, each represents a hydrogen atom, an alkyl group, a hydroxy group, a hydroxyalkyl group, a carboxyl group, a carboxyalkyl group, a formyl group, an acyl group, a pyridyl group or a quinolyl group, and each of a and b is an integer of from 1 to 3, with the proviso that a plurality of R1 or R2 may be the same as or different from one another.

8. The method for producing arylamine according to claim 7 wherein the cyclic nitrogen-containing compound is 2,2'-bipyridyl or 1,10-phenanthroline.

9. The method for producing arylamine according to claim 1 wherein the copper-containing catalyst is a ligand-linked copper salt represented by the following general formula (3):

$$[CuL_1]Xm \cdot nH_2O \tag{3}$$

wherein Cu represents a monovalent or divalent copper element, L represents a compound represented by the following general formula (4), l is an integer of from 1 to 6, X represents OH, Cl, Br, I, $NO_2$, $NO_3$, $SO_4$, $ClO_4$, $BF_4$, $BF_6$, $PF_6$, SCN, NCS or $S_2O_8$, m is a natural number of from 0 to 2 and n is a natural number of from 0 to 10,

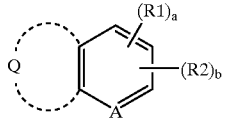

(4)

wherein A represents a nitrogen atom or an N-oxide (N→O), Q is not present or Q represents an atomic group which forms, together with the ring containing A, a five-membered or six-membered ring, R1 and R2, which may be the same as or different from each other, each represents a hydrogen atom, an alkyl group, a hydroxy group, a hydroxyalkyl group, a carboxyl group, a carboxylalkyl group, a formyl group, an acyl group, a pyridyl group or a quinolyl group, and each of a and b is an integer of from 1 to 3, with the proviso that a plurality of R1 and R2 may be the same as or different from one another.

10. The method for producing arylamine according to claim 9 wherein the ligand-linked copper salt is selected from picolinic acid copper salts and quinolinic acid copper salts.

11. The method for producing arylamine according to claim 1 wherein the copper-containing catalyst is a ligand-linked copper salt represented by the following general formula (5):

$$[CuL_1]Xm \cdot nH_2O \tag{5}$$

wherein Cu represents a monovalent or divalent copper element, L represents a compound represented by the following general formula (6), l is an integer of from 1 to 6, X represents OH, Cl, Br, I, $NO_2$, $NO_3$, $SO_4$, $ClO_4$, $BF_4$, $BF_6$, $PF_6$, SCN, NCS or $S_2O_8$, m is a natural number of from 0 to 2 and n is a natural number of from 0 to 10,

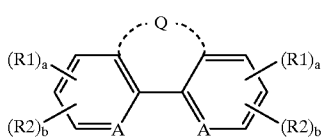

(6)

wherein A represents a nitrogen atom or an N-oxide (N→O), Q is not present or Q represents an atomic group which forms, together with the rings containing A, a five-membered or six-membered ring, R1 and R2, which may be the same as or different from each other, each represents a hydrogen atom, an alkyl group, a hydroxy group, a hydroxyalkyl group, a carboxyl group, a carboxylalkyl group, a formyl group, an acyl group, a pyridyl group or a quinolyl group, and each of a and b is an integer of from 1 to 3, with the proviso that a plurality of R1 and R2 may be the same as or different from one another.

12. The method for producing arylamine according to claim 11 wherein the ligand-linked copper salt is selected from 2,2'-bipyridyl copper salts.

13. The method for producing arylamine according to claim 5 wherein the cyclic nitrogen-containing compound is a compound selected from the group consisting of γ-picoline, 2-4-lutidine, 2,4,6-collidine, picolinic acid, quinolinic acid, 2-pyridylacetic acid, pyridine-2-aldehyde, 2-pyridine-methanol, 2-pyridineethanol, 2-hydroxypyridine, quinoline, quinaldine, 4-methylquinoline, 8-quinolinol, and quinaldic acid.

* * * * *